(12) United States Patent
Kusu et al.

(10) Patent No.: US 7,503,909 B2
(45) Date of Patent: Mar. 17, 2009

(54) INSTILLATION CONTAINER WITH LEVEL-DIFFERENCE PORTION

(75) Inventors: Yukio Kusu, Osaka (JP); Hiroshi Yamada, Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/493,877

(22) PCT Filed: Oct. 23, 2002

(86) PCT No.: PCT/JP02/11017

§ 371 (c)(1),
(2), (4) Date: Apr. 28, 2004

(87) PCT Pub. No.: WO03/037245

PCT Pub. Date: May 8, 2003

(65) Prior Publication Data

US 2004/0210203 A1 Oct. 21, 2004

(30) Foreign Application Priority Data

Oct. 31, 2001 (JP) ............................. 2001-334347

(51) Int. Cl.
*A61M 35/00* (2006.01)
*B65D 47/18* (2006.01)
(52) U.S. Cl. ...................... 604/298; 604/295; 222/420
(58) Field of Classification Search ......... 604/295–300; 222/420–421; 215/381–382, 384
See application file for complete search history.

(56) References Cited

U.S. PATENT DOCUMENTS

| 2,249,832 | A | * | 7/1941 | Hubschman ................. 222/420 |
| 3,945,381 | A | | 3/1976 | Silver |
| 4,605,398 | A | | 8/1986 | Herrick |
| 4,723,687 | A | | 2/1988 | Kutterer |
| 5,076,474 | A | | 12/1991 | Hansen |
| 5,261,572 | A | * | 11/1993 | Strater ........................ 222/215 |
| 5,464,122 | A | | 11/1995 | Lifshey |
| 5,718,334 | A | | 2/1998 | Demel |
| 5,954,233 | A | * | 9/1999 | Kawashima et al. .......... 222/83 |
| 6,129,248 | A | * | 10/2000 | Hagele ........................ 222/420 |

(Continued)

FOREIGN PATENT DOCUMENTS

EP 0 312 725 4/1989

(Continued)

OTHER PUBLICATIONS

Japanese Search Report issued Nov. 1, 2006.

*Primary Examiner*—Tatyana Zalukaeva
*Assistant Examiner*—Melanie J Hand
(74) *Attorney, Agent, or Firm*—The Webb Law Firm

(57) ABSTRACT

An eyedropper including a container and a cap which can be screwed onto the container unit wherein a tubular fluid instilling portion is provided at a tip of the container. An outer circumferential region of the tubular fluid instilling portion is provided with a step portion where the outer diameter of the container is smaller and whose outer diameter is substantially not reduced or changed moving towards the tip. The cap is provided with a convex seal portion, which, in the mounted condition, is in close contact with the tip and the step portion.

13 Claims, 11 Drawing Sheets

U.S. PATENT DOCUMENTS 6,168,581 B1 * 1/2001 Buehler .................. 604/295
6,334,557 B1 * 1/2002 Yang ..................... 222/567

FOREIGN PATENT DOCUMENTS

| | | | |
|---|---|---|---|
| EP | 0312725 | | 4/1989 |
| EP | 0362911 A1 | * | 8/1989 |
| EP | 362911 A1 | * | 4/1990 |
| EP | 0362911 A1 | * | 4/1990 |
| EP | 0 416 694 | | 3/1991 |
| EP | 0 425 263 | | 5/1991 |
| EP | 0459498 A1 | * | 12/1991 |
| EP | 0 639 510 | | 2/1995 |
| GB | 2020255 A | * | 11/1979 |
| HU | 206453 | | 7/1992 |
| JP | 555936/1977 | | 11/1978 |
| JP | 01 146552 | | 6/1989 |
| JP | 2-52758 | | 4/1990 |
| JP | 4-117636 | | 10/1992 |
| JP | 60-86341 | | 3/1994 |
| JP | 07-275322 | | 10/1995 |
| JP | 09 290456 | | 11/1997 |
| JP | 10 236493 | | 9/1998 |
| JP | 10-329855 | | 12/1998 |
| JP | 2000 190998 | | 7/2000 |
| JP | 2001-120639 | | 5/2001 |
| JP | 2001-120638 | | 8/2001 |
| JP | 2001-120639 | | 8/2001 |
| WO | WO 96/00173 | | 1/1996 |
| WO | WO 99/23006 | | 5/1999 |
| WO | WO 99/57030 | | 11/1999 |
| WO | WO 9957030 A1 | * | 11/1999 |

* cited by examiner

FIG.5
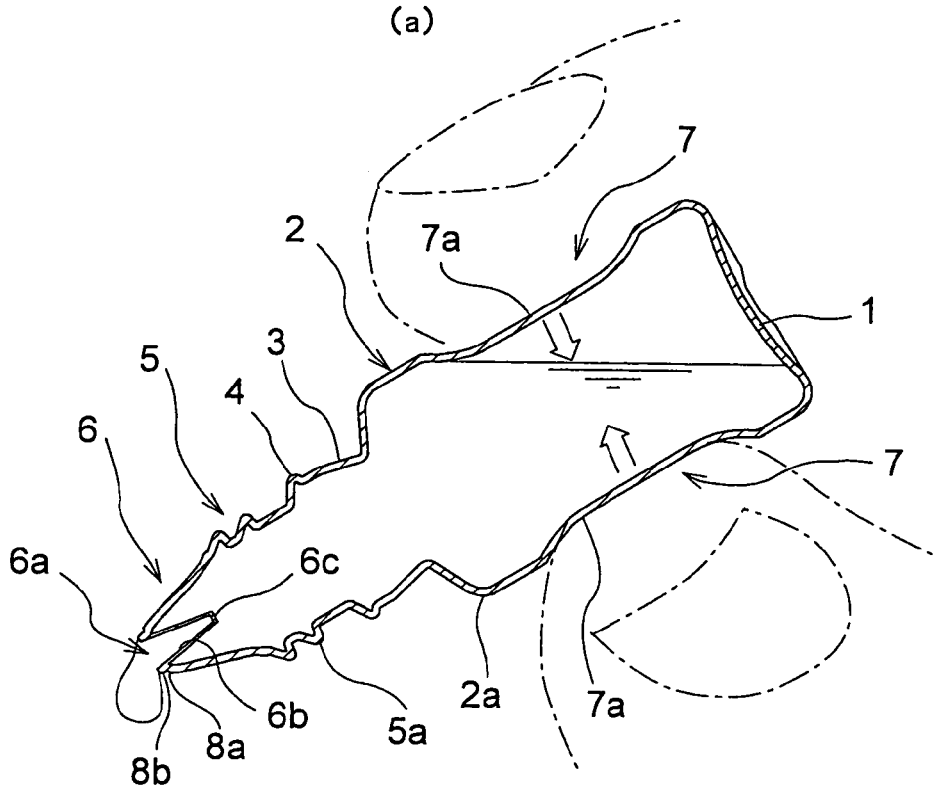
(a)
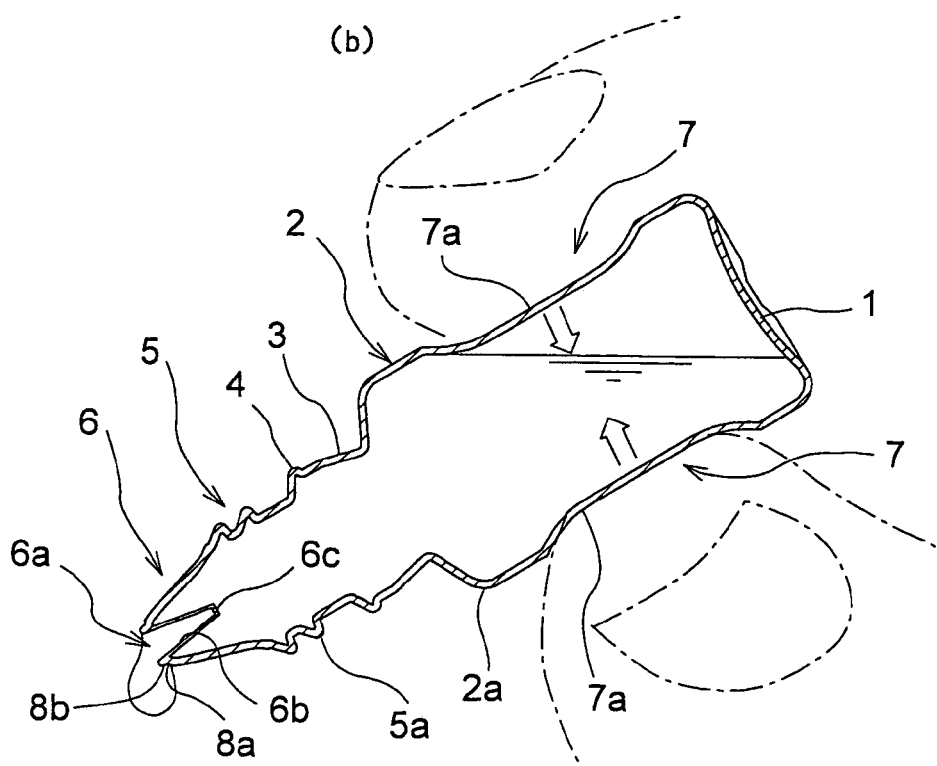
(b)

INSTILLATION CONTAINER WITH LEVEL-DIFFERENCE PORTION

BACKGROUND OF THE INVENTION

1. Field of the Invention

The present invention relates to an eyedropper comprising a container unit made of a thermoplastic material, and a cap which can be. screwed onto the container unit, wherein a tubular fluid instilling portion, which is provided at a tip portion of the container unit, is depressed into a bottomed conical concave portion whose internal diameter widens towards the tip side, wherein a instilling hole is formed or can be formed into the bottom of this concave portion, and wherein the cap is provided with a first convex sealing portion, which, when mounted, seals the concave portion of the container unit.

2. Description of the Related Art

Eyedroppers of this type have been proposed recently by the applicant of the present application (see JP 2001-120639A), such as an eyedropper in which a instilling hole is pierced in advance, or an eyedropper which uses a instilling hole formed just before use of the eyedropper. Indented portions are provided in the trunk portion of this eyedropper to make eye drop administration easier for the user.

A characteristic feature of this related art is that a concave portion is indented in the tip of the container unit, and that a instilling hole is formed or can be formed in the bottom of this concave portion.

As described in that specification, the amount of fluid squeezed from the container unit can be controlled and adjusted to an appropriate set volume by adjusting appropriately the diameter of the instilling port at the tip of the concave portion and the diameter of the instilling hole and the like.

With the eyedropper configured as above, the predetermined object may be achievable, however it has become clear that there is room for improvement with regard to the sealability of the pharmaceutical fluid sealed in the container unit, and further, with regard to preventing fluid from dribbling down the outer circumferential region of the tubular fluid instilling portion.

Explaining this in further detail, there is the possibility of a reduction in sealability between the cap and the container if the cap is repeatedly closed with excessive force, for example, or further if it is subject to excessive vibration when only a first convex sealing portion is provided opposite the concave portion provided in the container unit in the cap of the eyedropper in which the instilling hole has been pierced in advance.

On the other hand, when using a hole that is pierced at the time of use, without piercing the instilling hole in advance, the pharmaceutical fluid may spread to the outer circumferential region of the tubular fluid instilling portion and there is the possibility of the occurrence of what is known as fluid dribble. A solution to this problem is desired.

SUMMARY OF THE INVENTION

With consideration to the situation given above, it is a main object of the present invention to provide an eyedropper that will improve further the sealability between the cap and the container unit when the cap is screwed onto the container unit, and that when administering eye drops can prevent fluid dribble onto the outer circumferential region of the tubular fluid instilling portion.

In a characteristic configuration of the eyedropper of the present invention, an outer circumferential region of the tubular fluid instilling portion a step portion is provided where the outer diameter of the container unit is smaller on the tip side, and, on the tip side of the step portion, a tip protrusion portion whose outer diameter is substantially not reduced or changed towards the tip, and the cap is provided with a second convex sealing portion, which, in the mounted condition, is in close contact with the tip protrusion portion and the step portion.

Here, the term "whose outer diameter is substantially not reduced or changed towards the tip" means a condition in which the tip protrusion portion is perpendicular or substantially perpendicular with respect to the step portion.

According to this configuration, a step portion is provided on the outer circumferential region of the tubular fluid instilling portion positioned at the tip end of the container unit, and the portion from this towards the tip side is taken as the tip protrusion portion.

And, when the cap is mounted, the second convex sealing portion is in close contact with both of these portions and the first convex seal portion fits into and seals the concave portion provided in the tubular fluid instilling portion. Consequently, air sealability can be raised because the tip protruding portion is constructed to be held on both sides in its thickness direction (horizontal direction in FIG. 2 and FIG. 3).

Furthermore, when such a step portion is provided, this step portion can play a role in achieving clean drop delivery when the eyedropper is inclined to administer a drop into the eye as shown in FIG. 5.

Furthermore, fluid dribble onto the outer circumferential region of the tubular fluid instilling portion can be suitably prevented by providing a tip protrusion portion whose outer diameter is substantially not reduced or changed towards the tip.

In addition to the characteristic features described above, the following advantages are attained when a third convex guide portion is arranged at a certain spacing at a radially outward position with respect to the second convex seal portion, the third convex guide portion extending towards the container unit side when in the mounted position and guides the cap when the cap is mounted.

That is to say, by providing such a third convex guide portion, the container unit and the cap can be screwed together while matching the axes of the container unit and the cap.

Furthermore, it is preferable that a distance from the tip to the step portion of the container unit is selected in a range of 0.2 to 1.2 mm, and that the step portion has a step difference in a range of 0.2 to 0.4 mm.

Here, the user may be frightened when administering the eye drops if the step gets large and the tip protrusion portion becomes long and pointy. Furthermore, when the cap is screwed on, there is a possibility of breakage if the tip protrusion portion becomes long and pointy and its strength becomes weak, and without screwing with sufficient strength it is possible that the air seal cannot be maintained.

Furthermore, a single drop of eye drop fluid is normally approximately 25 to 50 microliters. It has become clear to the inventors that the above ranges are preferable, based on results enquiring into the relationship of the above dimensions with this aim in mind.

That is to say, if the distance between the step portion and the tip of the container unit is smaller than the above range, the result is the same as providing no step portion. On the other hand, if it is made larger than the above range, a situation results in which the desired object cannot be attained.

This is also substantially the same with regard to the step difference given above. If the step difference is smaller than the above range, the result is the same as providing no step difference. On the other hand, if it is made larger than the above range, a situation results in which the desired object cannot be attained.

Furthermore, it is preferable that the container unit is filled in a sealed state with fluid, simultaneously to being molded.

According to the above configuration, by simultaneously sealing, a reduction of the manufacturing cost in particular can be attained.

Furthermore, it is preferable that the depth of the concave portion is in a range of 2 to 7 mm.

If the concave portion depth becomes less than these appropriate values, then the problem may occur that the tip portion of that concave portion, in other words the instilling port, is covered by liquid accumulated by surface tension in the annular space (liquid pool) formed at the periphery of the concave portion of the container, and the liquid in that pool is squirted through the instilling port by the pressure generated when the container is picked up by hand.

Furthermore, if the concave depth is larger than the appropriate values, then the occurrence of defects, such as cracks in the concave portion, becomes more likely during the process of forming this concave portion. The optimum value that satisfies these conflicting conditions is 6 mm.

However, if the pharmaceutical fluid has a low surface tension, then the amount of liquid accumulated is reduced and there is not such a necessity for concave portion depth, so that in this case, it is also possible to design the concave portion with a shallow depth.

Furthermore, it is preferable that the opening diameter at the tip of the concave portion is configured in a range of 2 to 4 mm.

According to this configuration, in order to standardize the volume of a single drop (adjusted, depending on the object, to within a range of 25 to 50 microliters per drop), the opening diameter is reduced for liquids with high surface tension, and the opening diameter is enlarged for liquids with low surface tension.

Furthermore, it is preferable that opposing indented portions are formed on the hollow tubular trunk portion of the container unit.

According to this configuration, the finger gripping position is made stable when administering the pharmaceutical fluid in the container since the indented portions formed in the trunk portion of the container are gripped with two finger tips. Moreover, when the trunk of the container is squeezed, because the one part of the trunk contacting those finger tips is already indented, that squeezing force can be reduced when compared to the case in which one part of a tubular trunk is deformed against the elastic restoration force.

Consequently, with the simple and cheap process modification of simply indenting the hollow tubular trunk portion, it is possible to make the eyedropper easier to hold and, due to a reduction of the required pressing force, improve its squeezability compared to conventional eyedroppers. Thus, an easy to use indented eyedropper with an indented portion can be provided, with which the pharmaceutical fluid in the container can be administered accurately and easily.

Furthermore, due to the reasons described below, it is advantageous if the cap is screwed onto the container unit in a condition in which the thermoplastic material has plasticity, forming the step portion with the second convex seal portion, and close contact is maintained between the tip protrusion portion, the step portion and the second convex seal portion.

With the above-described configuration, the shape of the tip protrusion portion and the step portion is determined when the container unit and the cap are screwed together, and these regions are reliably covered by the second convex seal portion of the cap, so that a reliable airtight condition can be achieved.

Further features and advantageous effects of the present invention will become apparent from the following detailed description taken in conjunction with the accompanying drawings.

BRIEF DESCRIPTION OF DRAWINGS

FIG. 5 is a drawing showing the usage condition when administering a drop.

DETAILED DESCRIPTION OF THE PREFERRED EMBODIMENTS

First Embodiment

FIG. 1 to FIG. 5 show an eyedropper of the present invention which is used principally for medical use, this eyedropper being configured from a flexible thermoplastic container unit A, formed by blow molding or vacuum molding into which is simultaneously filled a predetermined volume of pharmaceutical fluid, and a cap B, removably screwed onto a male thread 5a formed on a threaded cylindrical portion 5 of the container unit A.

Figure 1:
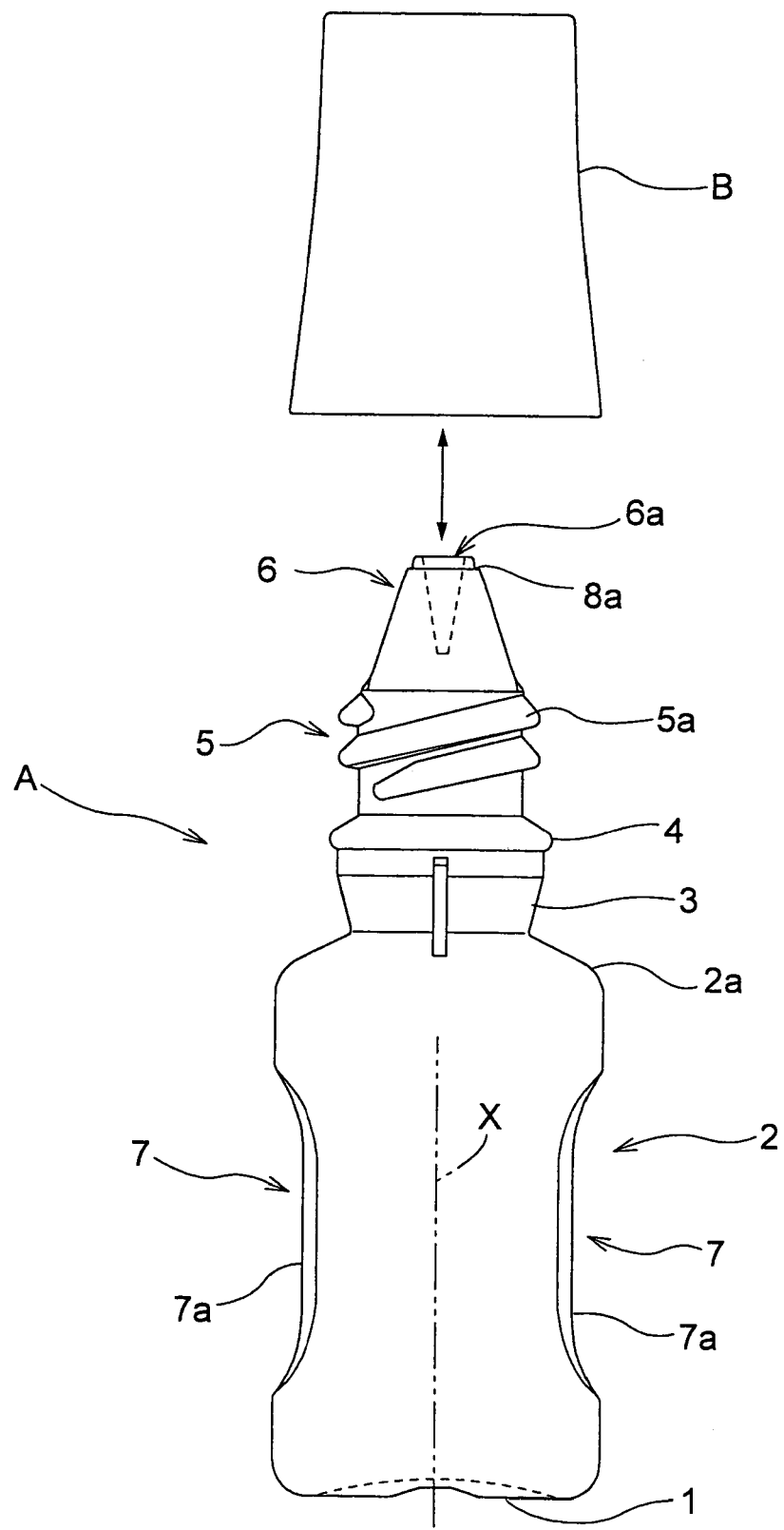
FIG. 1 is a drawing showing an outline of the eyedropper of the present invention.
Figure 2:
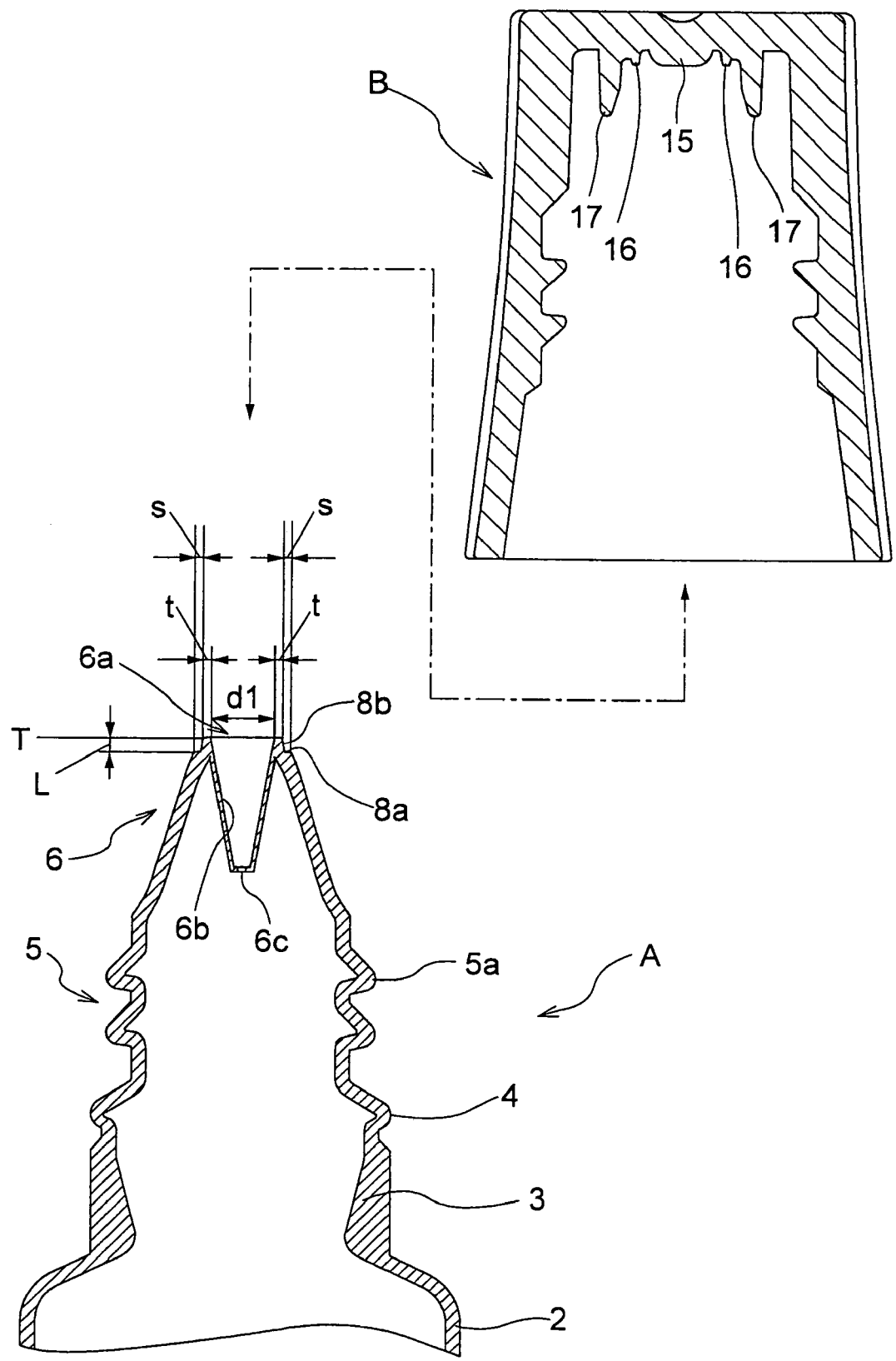
FIG. 2 is a front cross-sectional drawing showing the tip vicinity of the container unit in a condition in which the cap and the container unit are separated.
Figure 3:
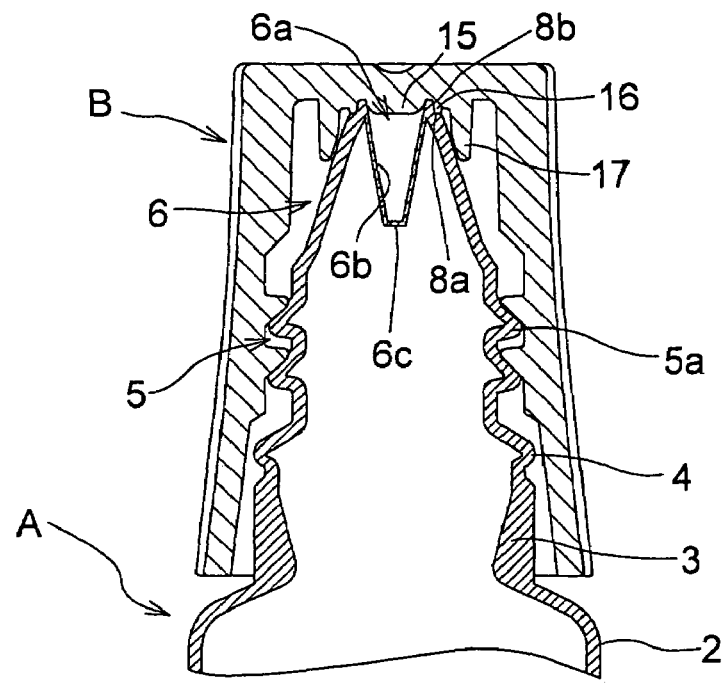
FIG. 3 is a front cross-sectional drawing showing the tip vicinity of the container unit, in a condition in which the cap is screwed onto the container unit.
Figure 4:
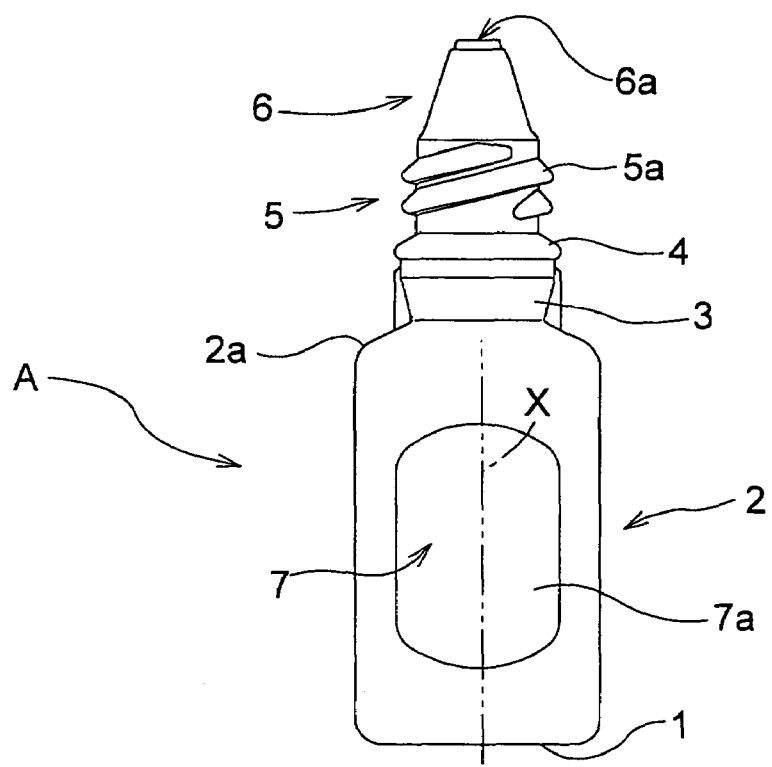
FIG. 4 is a full lateral view of the container unit.

Here, FIG. 1 is a figure showing an outline structure of the eyedropper of the present invention, FIG. 2 is a figure showing the condition of the container unit tip vicinity when the cap and container unit are separated, FIG. 3 is a figure showing the condition when they are screwed together, FIG. 4 is a lateral view of the overall container unit and FIGS. 5 (a) and (b) are figures showing the conditions during the act of drop instillation.

The container unit A is made of a round bottom portion 1 which is curved inward, a hollow cylindrical trunk portion 2 which is linked to its periphery, a cylindrical neck portion 3 which continues a shoulder portion 2a of the trunk portion 2, a stepped annular portion 4 swelling out in a diametrical direction from the upper side position of the neck portion 3, the threaded cylindrical portion 5 provided with the male thread 5a and formed in continuation with the upper side of the stepped annular portion, and a tubular fluid instilling portion 6 provided with a instilling port 6a and formed in continuation with the upper side of the threaded cylindrical portion.

Examples of the thermoplastic material serving as the structural material of the container unit A include polyethylene, polyethylene-polypropylene, polypropylene, polyethyethylene terephthalate, and polycarbonate and the like, and the overall container unit A is configured to allow elastic deformation.

As shown in FIG. 2, in the tubular fluid instilling portion 6 of the container unit A, a bottomed conical concave portion 6b, whose internal diameter is enlarged towards the instilling port 6a side (tip end), is formed as a depression, and a small diameter instilling hole 6c is formed in the bottom of this concave portion 6b.

The depth of the concave portion 6b is in a range of 2 to 7 mm, preferably in a range of 5 to 7 mm, and most preferably 6 mm, and the diameter of the instilling port 6a (diameter at mouth opening) is matched to the fluid properties of the pharmaceutical fluid, and adjusted within a range of φ 2 mm to φ 4 mm.

In order to fix the volume of a single drop (depending on its purpose, the volume of a single drop is adjusted within a range of 25 to 50 μL), if the surface tension of the liquid is large, the diameter of the instilling port 6a is decreased, and if the surface tension of the liquid is small, the diameter of the instilling port 6a is increased.

Furthermore, the instilling hole 6c is formed using a needle with a diameter in a range of φ 0.1 mm to φ 0.8 mm. The diameter of this needle is preferably small, and is most preferably about φ 0.2 mm, however if too small, it becomes technically difficult, so in practice a needle in a range of φ 0.4 mm to φ 0.6 mm is used.

Consequently, by setting the diameter of the instilling port 6a, the depth of the concave portion 6b and, furthermore, the diameter of the instilling hole 6c to suitable values, it is possible to control to a set amount the fluid drop volume squeezed from the container unit A by the pressing action of two finger tips on the trunk portion 2.

As shown in FIG. 2 and FIG. 3, in the circumferential region of the tubular fluid instilling portion 6 at the tip portion of the container unit A, a step portion 8a is provided, sharply reducing the external diameter in the tip direction of the container unit A, and, on the tip side of this step portion 8a in the tip direction, a tip protruding portion 8b is provided, which is provided with a circumferential surface that is substantially perpendicular to the step portion 8a. However, as this circumferential face is formed the first time the cap is tightened, there may be a slight incline discrepancy.

Here, a distance L from the tip T of the container unit A to the step portion 8a is in a range of 0.2 to 1.2 mm, most preferably selected as 0.7 mm, and with regard to this step portion 8a, the step s is in a range of 0.2 to 0.4 mm, most preferably selected as 0.3 mm. Furthermore, as opposed to the φ 2 mm to φ 4 mm opening diameter d1 of the concave portion 6b, the thickness t (in FIG. 2, the thickness in the horizontal direction) of the tip protruding portion 8b is in a range of 0.2 to 0.4 mm, and is most preferably selected as 0.3 mm.

As shown in FIG. 1 and FIG. 4, two indented portions 7 grippable by two finger tips are formed on the trunk portion 2 of the container unit A, and these indented portions 7 are configured from a pair of flat, or substantially flat gripping faces 7a, which have each been depressed at opposing positions on either side of a container axis X, at two places in the circumferential direction of the trunk portion 2.

Each of the gripping faces 7a, seen in the container axis X direction, are gently curved at a curvature that is less than the curvature of other parts of the trunk portion 2, and, seen in the radial direction (in the front view) perpendicular to the container axis X direction, the intermediate portion which excludes the end portions in the container axis X direction, is linear and parallel to the container axis X. Of course, it is also possible to entirely curve form this face.

The cap B is formed in one piece with a first convex seal portion 15, which fits into and seals the concave portion 6b of the container unit A when the cap B is screwed onto the male thread 5a of the container unit A.

The protrusion amount of this first convex seal portion 15 is approximately 0.6 to 1.0 mm.

As shown in FIG. 2 and FIG. 3, the cap is further provided with a second convex seal portion 16, which is in close contact with the protruding portion 8b and the step portion 8a provided on the container unit A when the cap is mounted. The protrusion amount of this second convex seal portion 16 is approximately 0.2 to 1.2 mm, its thickness is approximately 0.2 to 0.4 mm, and it is equivalent to the thickness of the step portion 8a.

Still further a third convex guide portion 17 extending towards the container unit side when mounted is provided at a certain spacing at a position on the outward radial side with respect to the second convex seal portion 16. When the cap B is mounted, this third convex guide portion 17 performs the function of guiding (ensuring good posture) the cap B with respect to the container unit A as shown in FIG. 3. Consequently, by providing this third convex guide portion 17, at the time of first mounting of the cap B onto the container unit A as mentioned later, it becomes possible to appropriately match an axial line of the container unit A and an axial line of the cap B with the container axis X, and it becomes possible to carry out satisfactorily the formation of the step portion 8a and the tip protruding portion 8b.

Here, the protrusion amount of this third convex guide portion 17 is approximately 2.5 to 5.5 mm, and its thickness is approximately 0.5 to 1.2mm.

The material of the cap B is polypropylene, polyethylene or the like.

With the above configuration, it is possible to satisfactorily screw together and unite the cap B with the container unit A.

In the following, a second embodiment and a third embodiment of this application are explained with reference to FIG. 6 and FIG. 7, focusing on the container unit A. The second embodiment is an example in which the instilling hole 6c can be formed by piercing the container unit A and the third embodiment is an example in which a mid stopper 11 is provided.

Second Embodiment

Figure 6:
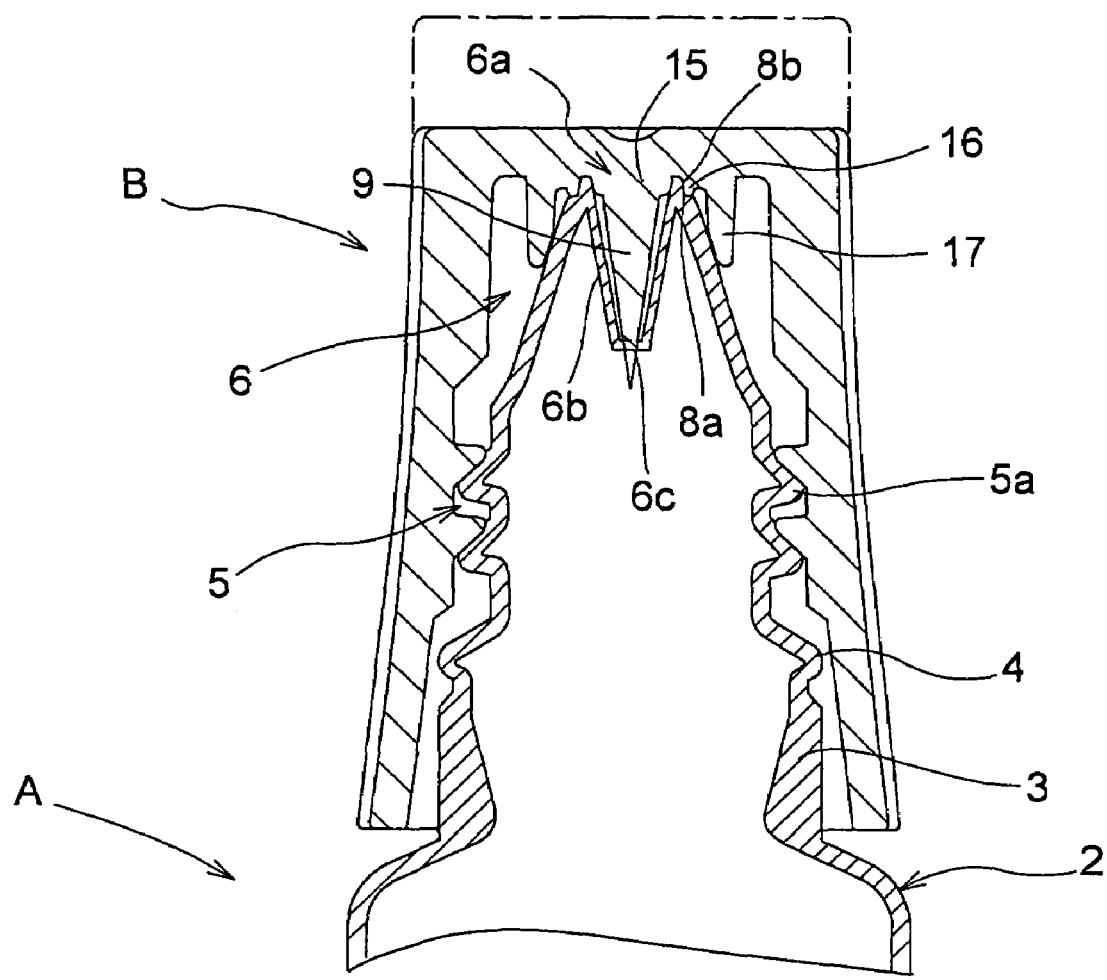
FIG. 6 is a lateral cross-sectional drawing of the container unit which is configured to allow the piercing of the instilling hole.

Each of the above embodiments explain an eyedropper, in which are preformed, at the tubular fluid instilling portion 6 of the blow molded or vacuum molded container unit A, a bottomed conical concave portion 6b whose internal diameter increases towards the instilling port 6a, and a small diameter instilling hole 6c by which it is possible to control to a set volume the drop volume squeezed from the container unit A by the action of finger tip pressure on the trunk portion 2, however, the invention of this application is not limited to such an eyedropper, but as shown in FIG. 6, may be configured so that, by screwing removably the cap B, which is formed unitarily with a needle-shaped projection 9 for piercing the instilling hole in the tip of the container unit A, onto the male thread 5a of the container unit A, which is made of a flexible thermoplastic material which has been blow molded or vacuum molded, and into which has been simultaneously filled and sealed a pharmaceutical liquid, the instilling hole 6c is formed in the tip portion of the container unit A by the needle-shaped projection 9 of the cap B by tightening the cap B to a position one step deeper than the normal stop position.

It should be noted that the rest of the configuration is the same as the configuration explained in the first embodiment, so that the same numerals as in the first embodiment are used for the same structures, which will not be explained further.

Third Embodiment

Figure 7:
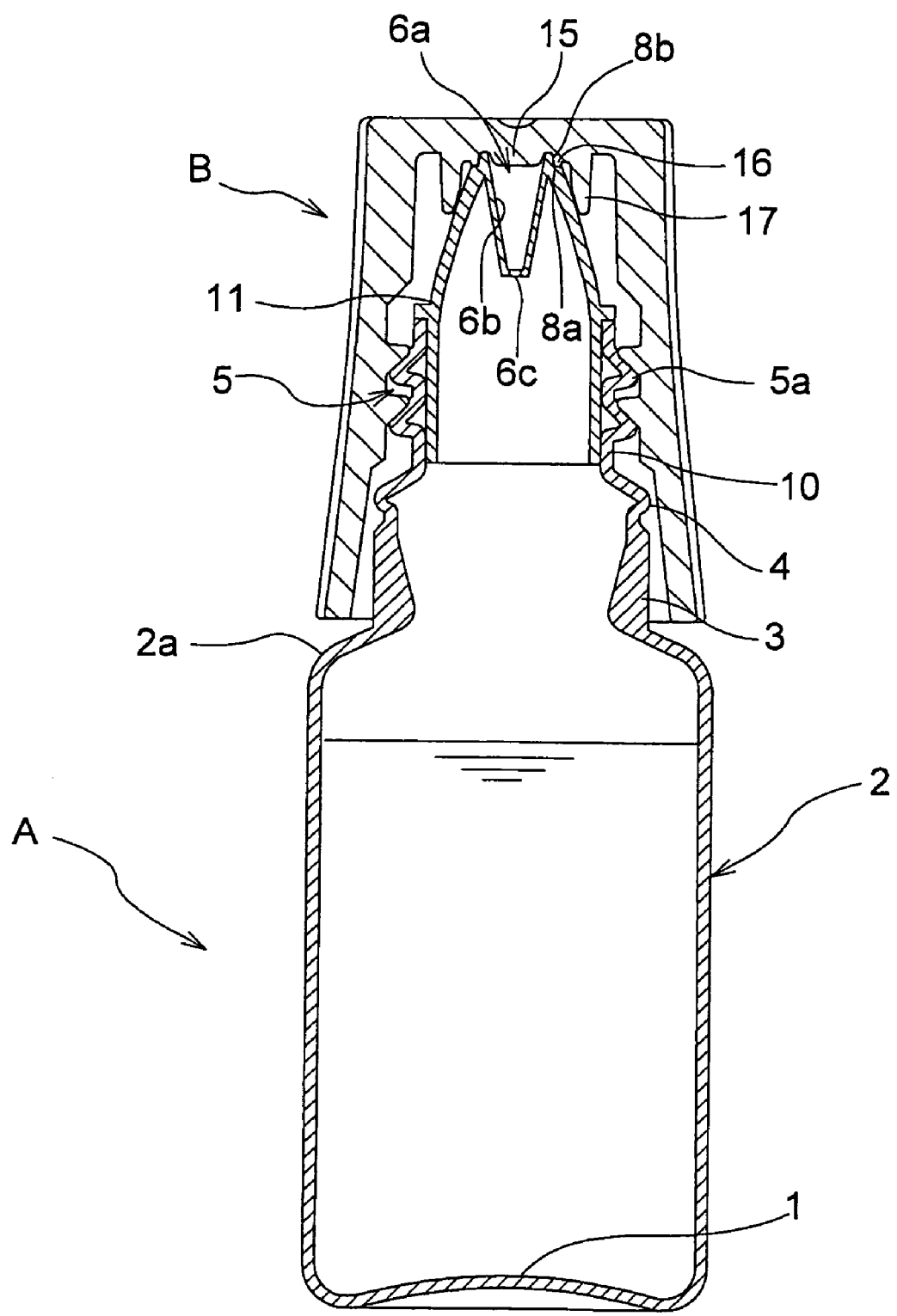
FIG. 7 is a figure showing an eyedropper container unit provided with a stopper.

In the above first and second embodiments, as the container unit A, an eyedropper, which has been molded while provided with a stopper capability, by blow molding or vacuum molding, has been illustrated, however the invention is not limited to eyedroppers with such a configuration, and as shown in FIG. 7, may be configured such that an injection molded stopper member 11 fits into a tubular mouth portion 10 of the container unit A.

It should be noted that the rest of the configuration is the same as the configuration explained in the first embodiment, so that the same numerals as in the first embodiment are used for the same structures, which will not be explained further.

Manufacturing Method of the Eyedropper

Below, a manufacturing method of the eyedropper of the present application will be explained in the order of manufacture of the container unit and unification with the cap.

I. Manufacture of the Container Unit

Figure 8:
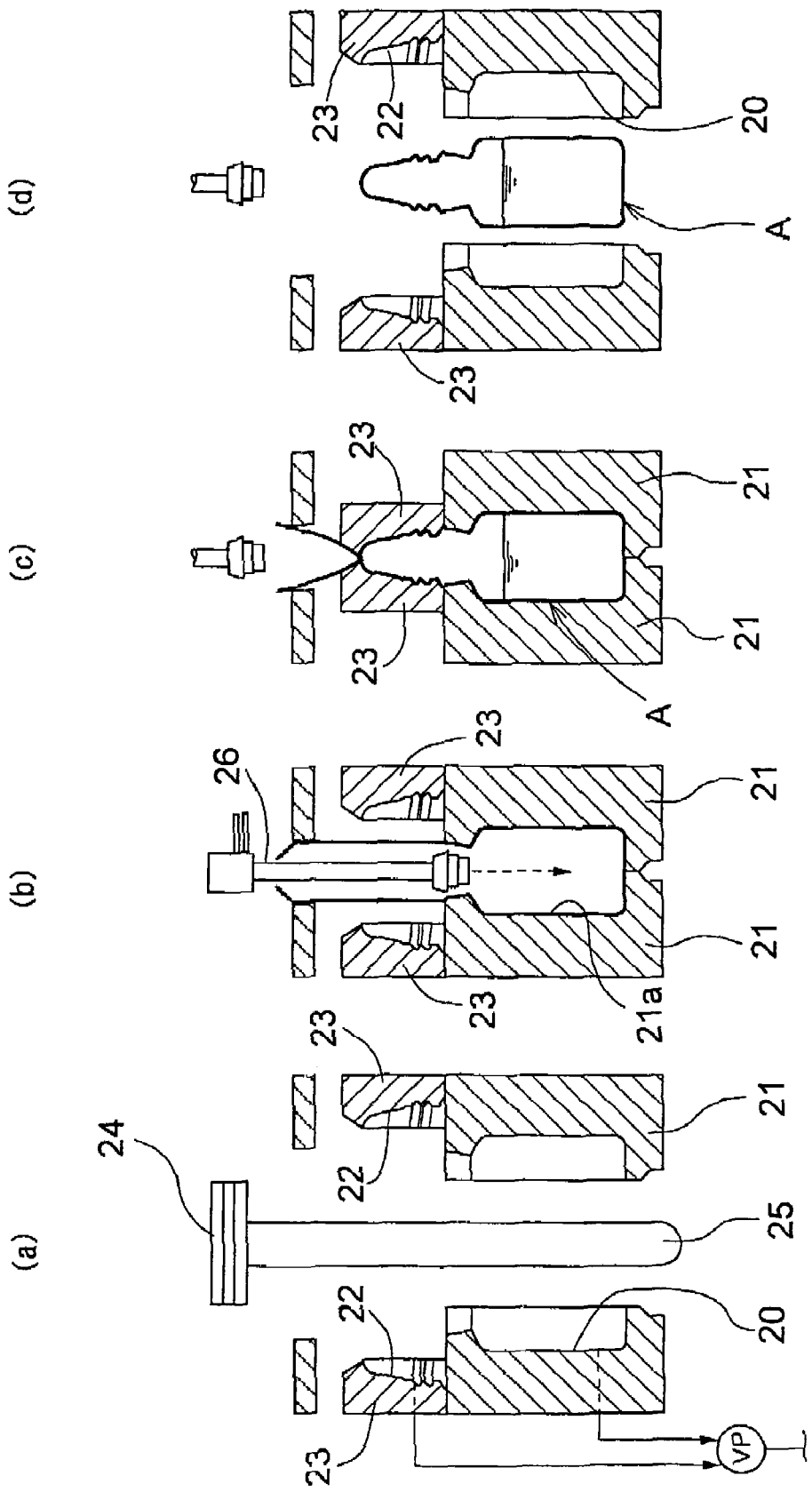
FIG. 8 is a molding process diagram in which the container unit is blow molded or vacuum molded.

A method for manufacturing the container unit A, in which the concave portion 6b and the instilling hole 6c have been formed, and before the step portion 8a and the protruding portion 8b are formed is already well known in the art, so that is explained in simple terms based on FIG. 8. In this explanation, the unit given above in the first embodiment is taken as an example of the shape of the container unit A As shown in FIG. 8(a), while the pair of main molds 21 which are provided with a first cavity 20 for the purpose of forming the portion of the container unit A in a range from the stepped annular portion 4 to the bottom portion 1, and the pair of sub molds 23 which are provided with a second cavity 22 for the purpose of forming the threaded cylindrical portion 5 and the tubular fluid instilling portion 6 of the container unit A, are in the open position, a slender hollow tube-shaped parison 25 of predetermined length and made of a half-melted thermoplastic material is extended from an extruder head 24 arranged above the same molds in a perpendicular direction along the molds 21 and 23.

Next, as shown in FIG. 8(b), molding is performed by expanding the parison 25 along a molding face 21a of the main molds 21 by closing the main molds 21 and blowing in compressed air or evacuating. In this condition, as shown in FIG. 8(b), a predetermined volume of liquid (pharmaceutical fluid) is filled from a pharmaceuticals supply pipe 26.

As shown in FIG. 8(c), once this liquid filling process has finished, molding is performed by expanding the parison 25 along a molding face 23a of the sub molds 23 by closing the sub molds 23 and blowing in compressed air or evacuating, simultaneously closing in (sealing) the liquid that has been filled. Then, the operation is concluded by the process in FIG. 8(d).

The following is an explanation of three manufacturing methods, in which the bottomed conical concave portion 6b and the small diameter instilling hole 6c are formed into the tubular instilling portion 6 at the tip of the container unit A that was blow molded or vacuum molded as described above.

First Manufacturing Method

A manufacturing method shown in FIGS. 9(a) to (d) uses a convex forming die 30 made of metal, which forms the bottomed conical concave portion 6b, and a needle-shaped forming die 31, which forms the instilling hole 6c.

The convex forming die 30 is configured such that a cone-shaped forming protrusion 30B for forming the bottomed conical concave portion 6b and a bowl-shaped (bell-shaped) molding face 30C for forming the outer circumferential face of the tubular fluid instilling portion 6 of the container unit A are formed on the tip of an attachment shaft 30A, and further, the needle-shaped forming die 31 is configured such that on the tip of the attachment shaft 31A a needle-shaped protrusion 31B for forming the small diameter instilling hole is formed.

Figure 9:
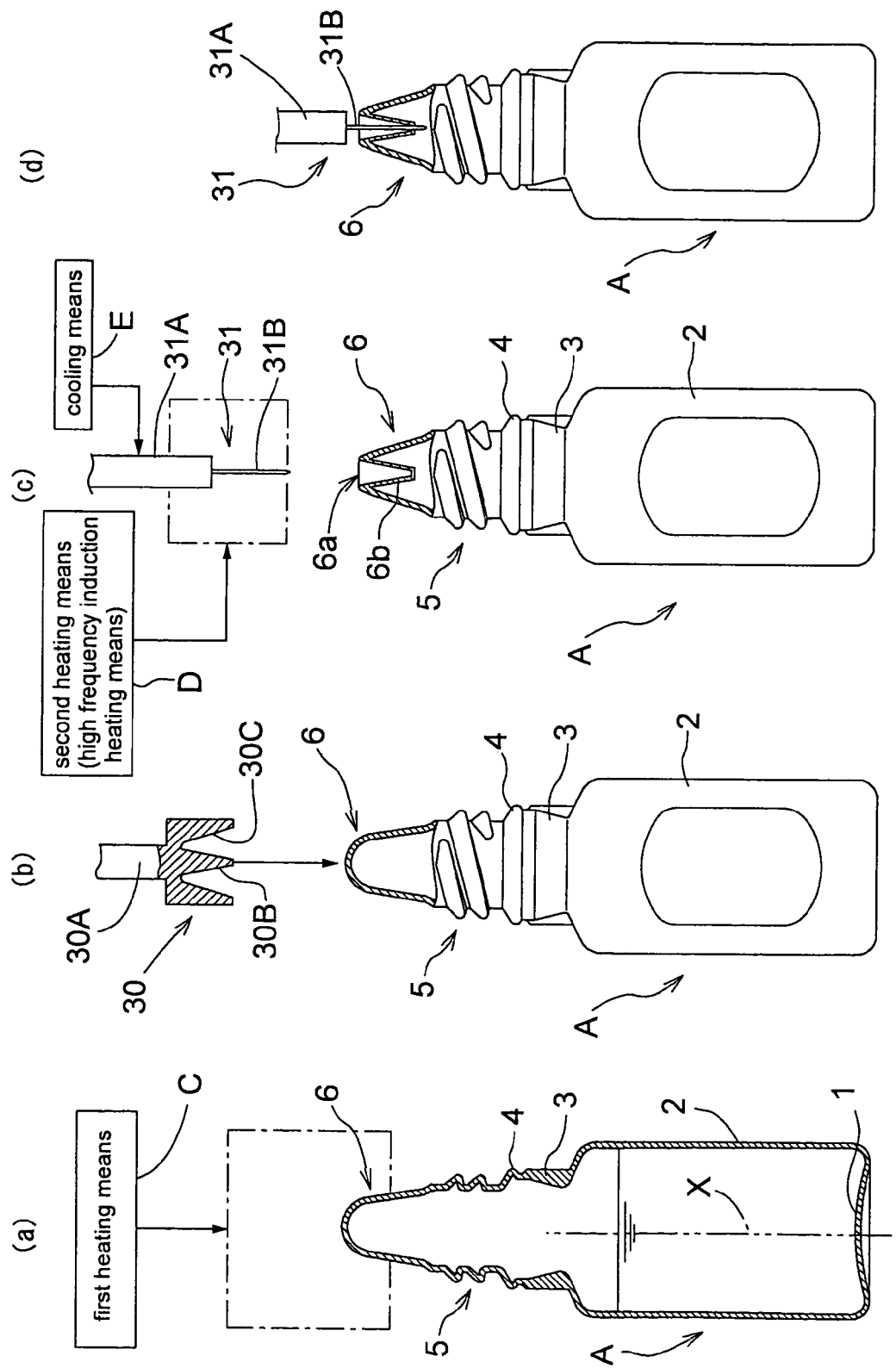
FIG. 9 is a process diagram illustrating a first manufacturing method.

And, in this first manufacturing method, as shown in FIG. 9(a), using a first heating means C of warm air, a halogen lamp, or laser light or the like, that part of the tubular fluid instilling portion 6 which is the tip portion of the container unit A is set to room temperature, or heated to 70° C. to 150° C. While the heating temperature will depend on the shape and material of the container unit A, a temperature that will slightly soften the tip of the container unit A is preferable.

If the thermoplastic material of the container unit A is a soft resin material such as polyethylene, the tip portion will buckle unless heated, so before forming it is necessary to heat at least the part to be formed by the convex forming die 30 with the first heating means C to a temperature that will prevent buckling. However, if the shape or resin material is able to withstand buckling, that is, if the pushing pressure from the container axis X direction of the convex forming die 30 is able to be resisted, then forming is also possible at room temperature.

Next, before the part of the tubular fluid instilling portion 6 of the container unit A that was heated by the first heating means C as shown in FIG. 9(b) cools, the convex forming die 30 is pressed down in the container axis X direction to form within the tubular fluid instilling portion 6 of the container unit A the bottomed conical concave portion 6b whose internal diameter widens towards the instilling port 6a end.

At this time, it is possible to remove the burrs from the time of blow molding which are protruding from the outer circumferential face of the tubular fluid instilling portion 6 of the container unit A with the bowl-shaped molding face 30C of the convex forming die 30.

The convex forming die 30 itself, matched to the shape and wall thickness of the tubular fluid instilling portion 6 of the container unit A to be formed, is temperature controlled in a range from room temperature to 150° C. It is preferable that the heating temperature is as low as possible, in consideration to cooling solidification of the tip of the tubular fluid instilling portion 6.

The convex forming die 30 can be easily exchanged, in accordance with the fluid properties of the fluid to be filled.

Next, as shown in FIGS. 9(c), (d), the needle-shaped forming die is pushed at the central bottom position of the concave portion 6b formed in the tubular fluid instilling portion 6 of the container unit A into the direction of the container axis X, forming the small diameter instilling hole 6c, which makes it possible to regulate the drop volume that is squeezed from the container unit A by the pressing operation of two finger tips on the trunk portion 2 to a set amount.

In the process of forming the instilling hole 6c with the needle-shaped protrusion 31B of the needle-shaped forming die 31, a method of working such that the needle-shaped protrusion 31B remains at room temperature, and a method such that work is done after heating of the needle-shaped protrusion 31 are proposed. The method that should be employed is to be selected with respect to conditions such as the formed shape of the instilling hole 6c, or the concave portion 6b, or further, the material and shape of the rest of the container, or the manufacturing cost and the like. If heating is required, it is preferable to set at least the temperature of the needle-shaped protrusion 31B of the needle-shaped forming die 31 in a range of 130° C. to 180° C., which is the melting temperature of the resin of the container material.

Heating of the needle-shaped forming die 31 is carried out by a second heating means D, such as high-frequency induction heating, halogen lamp or warm air or the like, and the attachment shaft 31A, which is the base of the needle-shaped forming die 31, is configured so as to cool the needle-shaped forming die by a cooling means E such as a water jacket or compressed air.

Once the needle-shaped forming die 31 has been cooled to a predetermined temperature, the needle-shaped forming die 31 is withdrawn in the direction from the container axis X from the tubular fluid instilling portion 6 of the container unit A that has been formed to a predetermined shape.

In order to ensure good resin separatability and mold release, it is also possible to surface treat the needle-shaped forming die 31 with surface plating, or teflon coating or special plating. For this surface treatment it is preferable that the coating is able to withstand high temperature, and will not easily strip off.

Second Manufacturing Method

In a second manufacturing method shown in FIGS. 10(a) to (d), similarly to the first method, a convex forming die 30 made of metal is used to form the bottomed conical concave portion 6b, and a needle-shaped forming die 31 made of metal is used to form the instilling hole 6c.

The convex forming die 30 is configured such that only a cone-shaped molding protrusion 30B for forming the bottomed conical concave portion 6b is formed on the tip of an attachment shaft 30A, and the needle-shaped forming die 31 is configured such that a needle-shaped protrusion 31B for forming the small diameter instilling hole and a bowl-shaped (bell-shaped) molding face 31C for forming the outer circumferential face of the tubular fluid instilling portion 6b of the container unit A are formed at the tip of the attachment shaft 31A. Still further, the base part 31b for attaching the needle-shaped protrusion 31B is formed in a conical shape following the concave portion 6b which was formed by the cone-shaped molding protrusion 30B.

Figure 10:
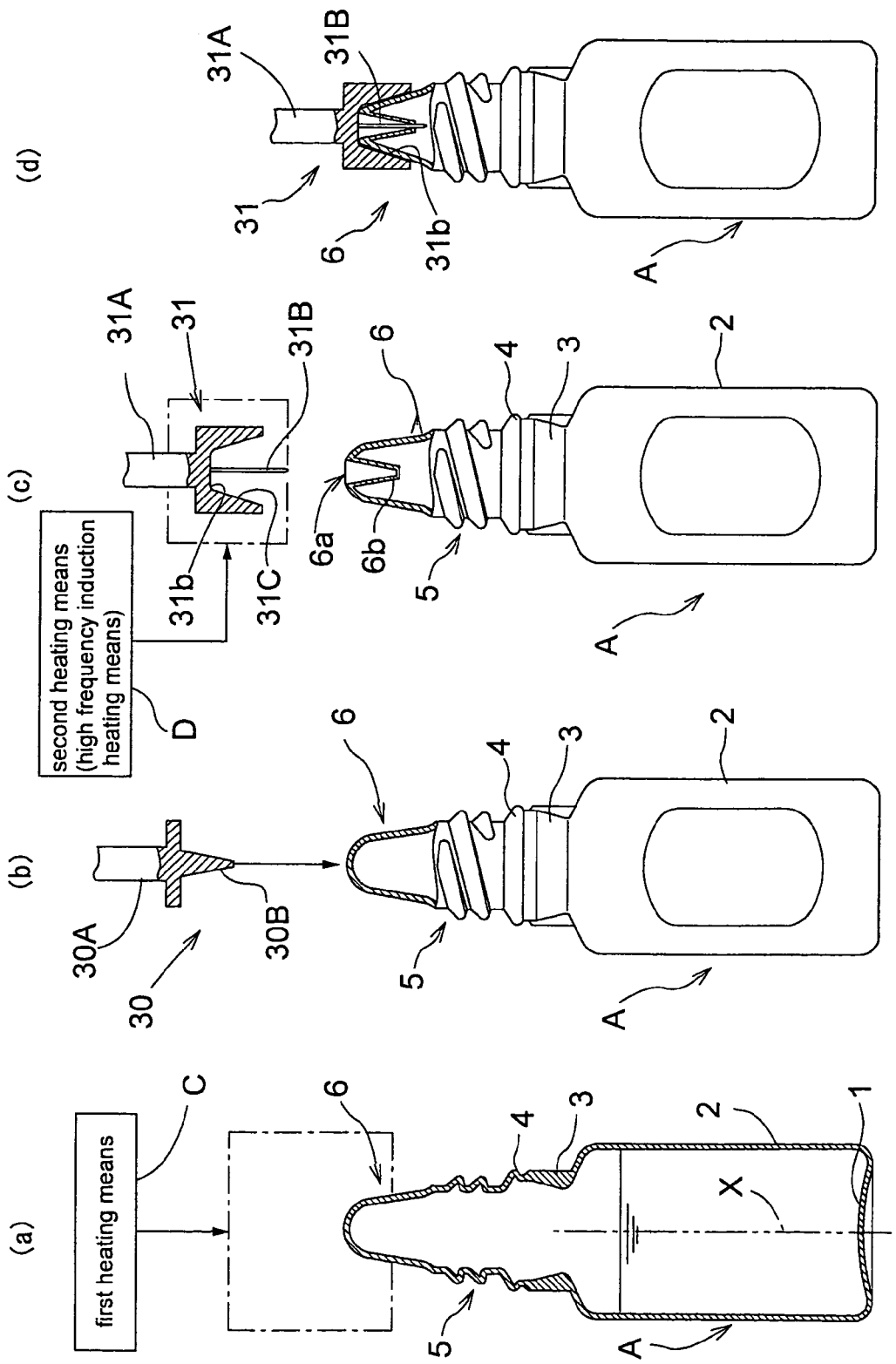
FIG. 10 is a process diagram illustrating a second manufacturing method.

In the first method, as shown in FIG. 9(b), the burrs from the time of blow molding protruding from the outer circumferential surface of the tubular fluid instilling portion 6 of the container unit A are removed when molding with the convex forming die 30, however in the second method, as shown in FIG. 10(c), the burrs from the time of blow molding protruding from the outer circumferential surface of the tubular fluid instilling portion 6 of the container unit A are removed when molding with the needle-shaped forming die 31, but the remaining configuration is the same as in the first method.

Third Manufacturing Method

In a third manufacturing method, shown in FIGS. 11(a) to (d), a single die 32 made of metal, which integrates the convex forming die which forms the bottomed conical concave portion 6b and the needle-shaped forming die which forms the instilling hole 6c, is used. This single die 32 is configured such that a cone-shaped forming protrusion 32B for forming the bottomed conical concave portion 6b and a bowl-shaped molding face 32D for forming the outer circumferential face of the tubular fluid instilling portion 6 of the container unit A are formed at the tip of an attachment shaft 32A, and an integrally formed needle-shaped protrusion 32C for forming the small diameter instilling hole 6c is formed coaxially at the tip of the cone-shaped forming protrusion 32B.

With this third manufacturing method, as shown in FIGS. 11(a), (b), the needle-shaped forming protrusion 32B forming the small diameter instilling hole 6c punctures the tip of the tubular fluid instilling portion 6 of the container unit A just prior to forming the concave portion 6b without heating the tip side of the tubular fluid instilling portion 6 of the container unit A, either at the molding temperature (70° C. to 80° C.) or after cooling to room temperature.

The needle-shaped forming protrusion 32C, which has punctured the tip of the tubular liquid instilling portion 6 of the container unit A as shown in FIG. 11(c), is heated by a high-frequency induction heating means, which is an example of a second heating means D. The heating temperature is preferably in the vicinity of the melting temperature of the container material, normally in a range of 120° C. to 200° C., and more preferably regulated to the vicinity of 160° C.

Figure 11:
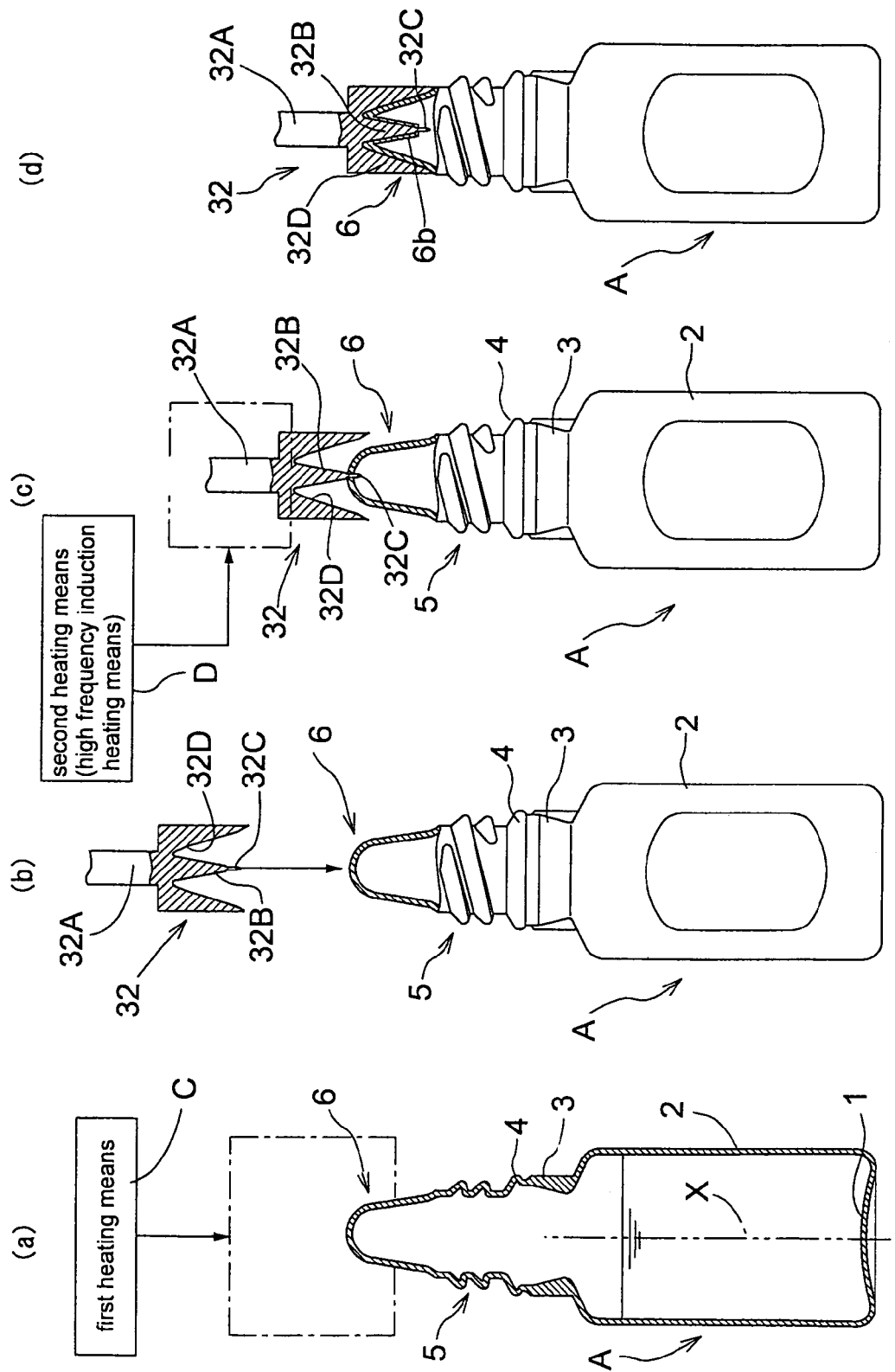
FIG. 11 is a process diagram illustrating a third manufacturing method.

The single die 32 provided with the needle-shaped forming protrusion 32C and the cone-shaped forming protrusion 32B, as shown in FIG. 11 (d), is pushed in from 2 mm to 8 mm while undergoing heating and, while pressing in the direction of the container axis X in such a way as to compress the tip side of the tubular fluid instilling portion 6 of the container unit A, forms the bottomed conical concave portion 6b.

It is preferable that the cone-shaped forming protrusion 32B of this single die 32 is pushed in as deeply as possible, however due to technical issues the depth is set in a range of 5 to 7 mm. At this time, it is also possible to provide a gas escape hole in the single die 32 so as not to allow air bubbles into the tip portion of the tubular fluid instilling portion 6 of the molten container unit A (as the resin at the tip portion is completely melted, a gas escape is required).

The attachment shaft 32A, which is the attachment base of the single die 32, is cooled by a cooling means such as a water jacket or compressed air.

And, once the single die 32 has been cooled to a predetermined temperature, the single die 32 is removed in the container axis X direction from the tubular fluid instilling portion 6 of the container unit A which has been formed to a predetermined shape.

In order to ensure good resin separatability and mold release, it is also possible to surface treat the single die 32 with surface plating, or teflon coating or special plating. For this surface treatment it is preferable that the coating is able to withstand at least 280° C., and that it is a coating that will not easily strip off.

The bottomed conical concave portion 6b and the small diameter instilling hole 6c on the tip portion side of the container unit A, which has been formed by one of the first to the third manufacturing methods, function as a stopper. Examples of this are a stabilized single drop volume, prevention of air bubble entrainment in the single drop of liquid, and improvement of air bubble elimination.

Furthermore, even in the above second and third methods, in the forming process of the instilling hole 6c by the needle-shaped forming protrusion 31B or 32C, work was performed after heating of the needle-shaped forming protrusion 31B or 32C by the second heating means D, however as mentioned previously, it is possible in some cases to form the instilling hole 6c using the needle-shaped forming protrusion 31B or 32C at room temperature without carrying out heating.

II. Unification With the Cap B

The container unit A can be obtained as described above, however, the cap B used in the present application as formed in the predetermined shape explained up to now must be obtained in advance.

Figure 12:
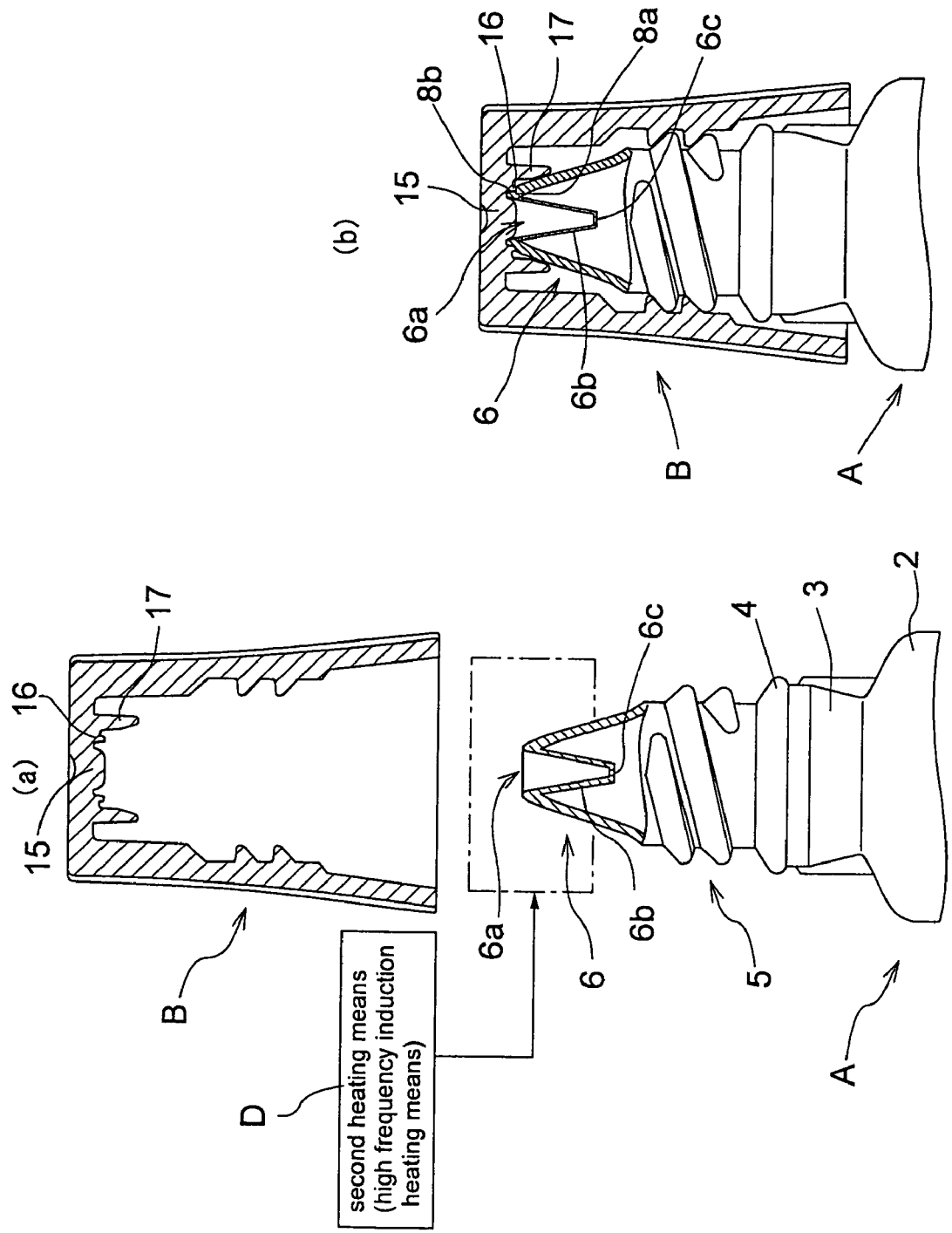
FIG. 12 is a process diagram in which the cap is first screwed on to the container unit.

So, after concluding the manufacture of the container unit A as described above, the thermoplastic material of the container A maintains its plasticity during the initial mounting, in which the cap is first mounted onto the container unit A, and the cap B is screwed onto the container unit A, as shown in FIG. 12, in a state in which the container unit A has such plasticity that the overall external shape of the container unit A will not collapse when the cap B is screwed on.

At this time, because the cap B is provided with a configuration that includes the first convex seal portion 15, the second convex seal portion 16 and the third convex guide portion 17, a condition is created where the first convex seal portion 15 is in close contact with the concave portion 6b, and the second convex seal portion 16 is in close contact with the tip protruding portion 8b and the step portion 8a. Furthermore, in practice, the shapes of the tip protruding portion 8b and the step portion 8a are determined by the first and second convex seal portions 15, 16, and the sealed condition is maintained.

Furthermore, as noted above, when the third convex guide portion 17 is screwed on, the axes of the container unit A and the cap B coincide neatly.

By employing the configuration given above, an easily useable eyedropper with excellent sealability can be obtained.

OTHER EMBODIMENTS (1) For the container unit A, it is possibly to use a container unit A having any kind of structure as long as at least the trunk portion 2 is configured in a hollow tubular shape with flexibility.

INDUSTRIAL APPLICABILITY

As explained above, the eyedropper according to the present invention is suitable to further improve sealability between the cap and the container unit when the cap is screwed on the container unit, and to prevent fluid dribbling down the outer circumferential region of the tubular fluid instilling portion when administering eye drops.

The invention claimed is

1. An eyedropper, comprising: a one piece plastic container having a seamless outer surface characteristic of blow-molding or vacuum-molding a one piece container, the container having a closed end, an instilling arrangement at the opposite end and external threads between the closed end and the instilling arrangement, of the container; the instilling arrangement comprising: a step having a step portion and a first tubular member, wherein the surface of the step portion faces away from the closed end of the container and the first tubular member has an external, generally conical convex surface; a second tubular member between the external threads and the step portion of the step, wherein the step is on an outer surface of the instilling arrangement and the outer surface of the second tubular member is an outer convex surface; a third tubular member connected to the first tubular member, wherein the juncture of the first and the third tubular members provides an exterior opening and the external, generally conical convex surface of the first member tapers to the exterior opening, the third tubular member extending away from the exterior opening into the second tubular member with end of the third tubular member spaced from the exterior opening providing an interior opening, wherein the third tubular member has an internal, generally conical concave portion that tapers to the interior opening and the third tubular member provides a fluid passageway from interior of the container to exterior of the container when the exterior and interior openings are open; and a cap, comprising: a body having a closed end, an opposite open end and internal threads, the interior of the body of the cap sized for the open end and body of the cap to move over the instilling arrangement of the container, and interior surface of the cap configured to provide a convex guide portion extending toward the open end of the cap and circumscribing internal portions of the cap, wherein the outer convex surface of the second tubular member guides the cap when the cap is mounted over the instilling arrangement, and with the cap over the instilling arrangement the internal portions of the cap are in sealing communication with the exterior opening to provide a first seal, and in surface contact with the surface of the step portion to provide a second seal, and the convex guide portion of the body of the cap contacts the outer surface of the second tubular member to guide the cap over the instilling arrangement.

2. The eyedropper according to claim 1, wherein a distance from the exterior opening to the surface of the step portion of the step of the instilling arrangement of the container is in a range of 0.2 to 1.2 mm, and the step portion has a step depth in a range of 0.2 to 0.4 mm, wherein the step depth is the distance from outer perimeter of the step portion to outer surface of the first tubular member.

3. The eyedropper according to claim 1, wherein the container has fluid, the instilling arrangement is uncovered and at least one of the exterior and interior openings of the instilling arrangement has a seal having a seamless connection with the at least one of the exterior and interior openings.

4. The eyedropper according to claim 1, wherein a depth of the third tubular member is in a range of 2 to 7 mm.

5. The eyedropper according to claim 1, wherein the exterior opening has a diameter in the range of 2 to 4 mm.

6. The eyedropper according to claim 1, wherein the container comprises opposing indented portions.

7. The eyedropper according to claim 1, wherein the plastic material is a thermoplastic material and the cap is screwed onto the instilling arrangement of the container and the step portion of the step is formed when the first and second tubular members are in a condition in which the thermoplastic material has plasticity.

8. The eyedropper according to claim 1, wherein the outer diameter of the second tubular member of the instilling arrangement decreases as the distance from the step portion of the step decreases, and outer diameter of the first tubular member of the step is substantially constant.

9. The eyedropper according to claim 1, wherein the container between the external threads and the closed end has a first body section having a predetermined outer diameter and a second body section having a predetermined outer diameter with the diameter of the first body section greater than the diameter of the second body section, and a shoulder portion interconnecting the first and second body sections of the container.

10. The eyedropper according to claim 9, wherein the container further comprises external threads on the second body section of the container adjacent the shoulder, and the cap further comprises internal threads on the internal surface of the body of the cap, and wherein with the internal and external threads fully engaged, the first and second seals are established and maintained.

11. The eyedropper according to claim 1, wherein the first seal comprises the cap having a conical-shaped member sized to extend into the third tubular member and extend beyond the interior opening of the instilling arrangement.

12. The eyedropper according to claim 1, wherein the second tubular member of the instilling arrangement has an outer surface and an opposite inner surface, and the third tubular member has a first surface facing and spaced from the inner surface of the second tubular member and an opposite second surface providing the fluid passageway between the exterior and interior openings.

13. The eyedropper according to claim 1, wherein outer perimeter of the second tubular member is greater than outer perimeter of the first tubular member, and the interior perimeter of the third tubular member has an increasing diameter as the distance from the interior opening increases.

* * * * *